United States Patent
Issleib et al.

(10) Patent No.: US 10,758,468 B2
(45) Date of Patent: Sep. 1, 2020

(54) SOLUBILIZER FOR COSMETIC PREPARATIONS

(71) Applicant: Symrise AG, Holzminden (DE)

(72) Inventors: Martina Issleib, Hoisdorf (DE); Jürgen Claus, Bevern (DE); William Johncock, Reinbek (DE); Rolf Ohrmann, Tostedt (DE); Martina König, Hamburg (DE)

(73) Assignee: Symrise AG, Holzminden (DE)

( * ) Notice: Subject to any disclaimer, the term of this patent is extended or adjusted under 35 U.S.C. 154(b) by 592 days.

(21) Appl. No.: 14/982,269

(22) Filed: Dec. 29, 2015

(65) Prior Publication Data

US 2016/0106650 A1 Apr. 21, 2016

Related U.S. Application Data

(62) Division of application No. 13/300,104, filed on Nov. 18, 2011, now abandoned.

(60) Provisional application No. 61/415,516, filed on Nov. 19, 2010.

(30) Foreign Application Priority Data

Nov. 19, 2010 (EP) .................... 10 191 925

(51) Int. Cl.
| | |
|---|---|
| *A61K 8/44* | (2006.01) |
| *A61K 8/34* | (2006.01) |
| *A61Q 19/00* | (2006.01) |
| *B01F 17/00* | (2006.01) |
| *A61K 8/04* | (2006.01) |
| *A61K 8/06* | (2006.01) |
| *A61Q 5/06* | (2006.01) |
| *A61Q 17/04* | (2006.01) |
| *A61Q 19/04* | (2006.01) |
| *A61Q 19/10* | (2006.01) |

(52) U.S. Cl.
CPC ............... *A61K 8/44* (2013.01); *A61K 8/042* (2013.01); *A61K 8/06* (2013.01); *A61K 8/345* (2013.01); *A61Q 5/06* (2013.01); *A61Q 17/04* (2013.01); *A61Q 19/00* (2013.01); *A61Q 19/002* (2013.01); *A61Q 19/004* (2013.01); *A61Q 19/04* (2013.01); *A61Q 19/10* (2013.01); *B01F 17/0021* (2013.01); *B01F 17/0042* (2013.01); *B01F 17/0092* (2013.01); *A61K 2800/30* (2013.01); *A61K 2800/49* (2013.01)

(58) Field of Classification Search
CPC ..................................................... A61K 31/33
USPC ................................................. 514/183, 170
See application file for complete search history.

(56) References Cited

FOREIGN PATENT DOCUMENTS

| | | |
|---|---|---|
| DE | 3 432 219 A1 | 3/1986 |
| DE | 10 2005 051 865 A1 | 4/2007 |
| EP | 2 366 376 A1 | 9/2011 |
| FR | 2 694 569 A1 | 2/1994 |
| JP | 2004-250332 A | 9/2004 |
| WO | 2005/046626 A2 | 5/2005 |
| WO | 2006/069953 A1 | 7/2006 |
| WO | 2008/046791 A1 | 4/2008 |

*Primary Examiner* — Layla Soroush
(74) *Attorney, Agent, or Firm* — Dilworth & Barrese, LLP

(57) ABSTRACT

The present invention relates to a mixture comprising (i) one or a plurality of 1,2-alkane diols with 5 through 8 carbon atoms and (ii) one or a plurality of ammonium-, sodium- or potassium-$R^{alk}$-sarcosinates, wherein the structural element $R^{alk}$ represents alkanoyl, alkenoyl or alkadienoyl with 12 through 22 carbon atoms, and optionally (iii) one or a plurality of sodium- or potassium-C10-C16-alkyl-sulfoacetates. The invention further relates to particular compositions and cosmetic preparations, in particular body care products, containing said mixture or composition and methods of production thereof. The present invention further relates to the use of said mixture as solubilizer and for increasing the transparency or decreasing the turbidity of a preparation containing one or a plurality of further organic substances.

17 Claims, No Drawings

SOLUBILIZER FOR COSMETIC PREPARATIONS

The present invention relates to a mixture comprising (i) one or a plurality of 1,2-alkane diols with 5 through 8 carbon atoms and (ii) one or a plurality of ammonium-, sodium- or potassium-$R^{alk}$-sarcosinates, wherein the structural element $R^{alk}$ represents alkanoyl, alkenoyl or alkadienoyl with 12 through 22 carbon atoms, and optionally (iii) one or a plurality of sodium- or potassium-C10-C16-alkyl-sulfoacetates. The invention further relates to particular compositions and cosmetic preparations, in particular body care products, containing said mixture or composition and methods of production thereof. The present invention further relates to the use of said mixture as solubilizer and for increasing the transparency or decreasing the turbidity of a preparation containing one or a plurality of further organic substances.

Cosmetic preparations or body care products are regularly cloudy, opal or transparent and are often in the form of emulsions.

Lipophilic substances, for example vitamins, perfume oils or UV filters, often can only be incorporated with difficulty in cosmetic preparations, in particular when the latter have a mainly polar character, for example owing to a correspondingly high proportion of water, or of water in combination with ethanol, glycerol and/or C1-C4-alkane diols. In such cases solubilizers are regularly used, which may be individual substances or mixtures with medium HLB values, which thus virtually form a bridge from the polar environment to the nonpolar substrate. The sulfonates of short-chain alkyl aromatics, for example toluene sulfonate or cumene sulfonate, are very effective hydrotropes, but owing to their inadequate dermocosmetic compatibility they are of no importance in the field of cosmetics. Other cosmetic solubilizers, such as special hydrophilized oils for example, are indeed dermocompatible, but do not possess sufficient dissolving power and/or have poor low-temperature behavior, i.e. show a tendency to clouding even at room temperature. For this reason there is, especially in the cosmetics industry, a desire for new solubilizers that are free from the disadvantages described above.

Emulsions are usually formed from two immiscible liquid phases. In the preparation of an emulsion, one phase is dispersed in finely-divided form in the other phase. There are two main types of emulsions, namely "water-in-oil" and "oil-in-water" emulsions. In an oil-in-water emulsion (O/W emulsion) the oil is the internal phase, which is dispersed in the external (water) phase. The properties of the corresponding emulsion are substantially determined by the external phase, so that water-in-oil emulsions behave rather as oils and oil-in-water emulsions behave rather as aqueous solutions.

Numerous emulsifiers, solubilizers and solubility promoters have already been described in the prior art.

WO 2004/075868 and WO 2007/147904 describe O/W emulsifiers based on potassium cetyl phosphate, hardened palm oil glycerides and cetyl alcohol.

DE 1 132 925 proposes certain salts of cyclohexylsalicylic acid or of hippuric acid as solubilizers for compounds that are sparingly soluble in water.

DE 1 198 476 relates to solubilizers for essential oils, to render them water-soluble. The solubilizers proposed there comprise, along with an alkoxylated glycerol partial ester, an alkoxylated ester of a dialkanolamine with a higher fatty acid.

DE 3432219 A1 describes solubilizers for perfume oils, which are addition products from 10 through 60 mol ethylene oxide on reaction products of epoxidized triglyceride oils with mono- or polyhydric alcohols with 1 through 6 carbon atoms. According to DE 3432219 A1, perfume oils, which regularly are or contain oil-soluble essential oils, are solubilized in aqueous cosmetic preparations, so that clear preparations containing perfume oil are obtained.

WO 01/90245 A1 discloses solubilizers for lipophilic substances containing (a) adducts of ethylene oxide on fatty alcohols, (b) adducts of ethylene oxide and propylene oxide on fatty alcohols, and (c) adducts of ethylene oxide on triglycerides. The solubilizers described in WO 01/90245 A1 are said in particular to have improved dissolving power with respect to substances such as perfume oils, vitamins, UV filters and the like, are liquid and clear at room temperature and have a cold cloud point below 10° C.

EP 1 588 693 A1 relates to certain solubilizers for organic UV filters, wherein the solubilizers have one or a plurality of aromatic rings as an essential structural element.

EP 2 008 708 A2 describes solubilizers with a clear appearance and very good dissolving power for lipophilic substances such as perfume oils, vitamins or UV filters. A solubilizer according to EP 2 008 708 A2 is liquid at room temperature and clear and contains a) one or a plurality of ethoxylated fatty alcohols, b) one or a plurality of ethoxylated triglycerides with particular acyl residues and c) water.

JP 2004-250332 A discloses shampoo preparations containing a combination of pentane-1,2-diol and/or hexane-1,2-diol and one or a plurality of surfactants, sodium lauryl sulfoacetate being named as a surfactant.

DE 10 2008 031 205 A1 relates to the use of natural 1,3-diols in hair treatment agents. The hair treatment agents described there can contain extremely varied surfactants from various surfactant classes, and the numerous anionic surfactants mentioned include, among others, C8-C24-acyl sarcosides and alkyl sulfoacetates with alkyl residues comprising 6 through 22 carbon atoms.

WO 2005/046626 relates to a make-up and/or lip care cosmetic comprising a fatty phase in the form of globules dispersed in an aqueous phase, and at least one agent having a tensing effect and/or film-forming effect, wherein the average size by number of said globules is less than or equal to 1000 nanometers.

WO 2006/069953 relates to synergistically active mixtures of straight-chain 1,2-alkanediols having 5 to 10 C atoms and their use as skin moisture-regulating compositions.

DE 10 2005 051 865 A1 discloses a cosmetic preparation in the form of an oil-in-water emulsion for cleaning skin and hair, comprising a lipid phase, one or more detersive surfactants selected from anionic, amphoteric and/or nonionic surfactants, and at least one 1,2-alkanediol with 5, 6, 7 or 8 carbon atoms.

FR 2694569 A1 describes a solid transparent hygiene article, containing, in combination with a dermatologically or cosmetically acceptable carrier, a mixture of (a) 5-50 parts by weight of a foaming surfactant, (b) 12-100 parts by weight of a component conferring transparency containing (b1) 5-65 parts by weight of an amide component, (b2) 2-15 parts by weight ethylene glycol and/or propylene glycol, and (b3) 5-20 parts by weight glycerine, and (c) 5-55 parts by weight of a component causing solidification and comprising a sodium, potassium or magnesium salt of a fatty acid and/or a water-soluble and/or hydrophilic amine.

Polyethylene glycols are also often used as solubilizers. These can, however, cause skin irritations and attack the protective film of the skin, so that the use of polyethylene glycols in cosmetic preparations, in particular for people with sensitive skin, is problematic.

The object of the present invention was to provide a component (single substance or mixture of substances) that provides improved solubility of sparingly or poorly water-soluble organic compounds in water, i.e. increases the solubility of said organic compounds.

The required component was to be liquid and clear at 25° C. and 1013 mbar. Furthermore, the component was to be colored as little as possible, preferably light yellow or ideally colorless.

Preferably the component should permit the production of preparations that are as transparent, i.e. clear, as possible, preferably transparent, aqueous cosmetic preparations, which furthermore provide good or improved storage stability of the corresponding cosmetic preparations, in particular with respect to their long-term stability.

In addition the component should if at all possible not have an unpleasant odor or should not impart an unpleasant odor to cosmetic preparations, preferably the component should at most have a slight intrinsic odor.

The required component should preferably be effective even when used at low dosage and should preferably be universally suitable for the production of cosmetic preparations of varying viscosity and preferably should have very good dermal compatibility.

Accordingly, the present invention relates to a solubilizer that is very suitable for the production of cosmetic preparations with good storage stability and moreover is, in a preferred embodiment, free from polyethylene glycol (PEG) and among other things therefore also has very good dermal compatibility.

According to a first aspect of the present invention, this object is achieved by a mixture comprising
(i) one or a plurality of 1,2-alkane diols with 5 through 8 carbon atoms,
(ii) one or a plurality of ammonium-, sodium- or potassium-$R^{alk}$-sarcosinates, wherein the structural element $R^{alk}$ represents alkanoyl, alkenoyl or alkadienoyl with 12 through 22 carbon atoms, preferably with 16 through 22 carbon atoms, and
(iii) optionally one or a plurality of sodium- or potassium-C10-C16-alkyl-sulfoacetates
preferably with the proviso that the mixture is not a creme for the lips having the following composition:

| | |
|---|---|
| water | 60. 05 wt.-% |
| methylparabene | 0.2 wt.-% |
| Sorbitan tristearate (Span 65) | 1 wt.-% |
| Cetyl alcohol | 4.7 wt.-% |
| Glycerol mono/di/tri stearopalmitate | 3.9 wt.-% |
| PEG stearate, 40 EO (Myrj 52P) | 2.22 wt.-% |
| Potassium hexadecyl phosphate (Amphysol K) | 0.83 wt.-% |
| Isoparaffin oil | 4.7 wt.-% |
| Di isostearyl malate | 7 wt.-% |
| PDMS 5 cst | 5 wt.-% |
| propylparabene | 0.1 wt.-% |
| Decandiol and PEG-Ethers | 10 wt.-% |
| perfum | 0.3 wt.-% |
| methylparabene | 0.23 wt.-% |
| glycerin | 7.50 wt.-% |
| 1,2 pentanediol | 3.00 wt.-% |
| sodium palmitoyl sarcosinate | 0.50 wt.-% |
| pigments | 3.24 wt.-% |
| sodium saccharinate | 0.02 wt.-% |
| water | 5.00 wt.-% |

-continued

| | |
|---|---|
| STEARETH-100/PEG-136/HMDI Copolymer (Serad FX) | 0.50 wt.-%. |

A mixture according to the invention is not the mixture disclosed in WO 2005/046626, pages 62-63, example 1.

Preferably for a mixture according to the invention the proviso applies that
(i) if the mixture comprises 1,2-pentanediol, the concentration of 1,2-pentanediol is 4 wt.-% or more, preferably 5 wt.-% or more
and/or
(ii) if the mixture comprises sodium palmitoyl sarcosinate, the concentration of sodium palmitoyl sarcosinate is 1 wt.-% or more, preferably 5 wt.-% or more
wherein the percentages by weight refer in each case to the total mass of the mixture.

Particularly preferably for a mixture according to the invention the proviso applies that if the mixture comprises both, 1,2-pentanediol and sodium palmitoyl sarcosinate, the mixture additionally comprises
(i) one or more further 1,2-alkanediols having 5 to 8 C-atoms which are not 1,2-pentanediol and/or
(ii) one or more ammonium-, sodium- or potassium-$R^{alk}$-sarcosinates as defined above which are not sodium palmitoyl sarcosinate.

Particularly preferred according to the invention is a mixture as defined above which comprises at most one, preferably no substance selected from the group consisting of 1,2-pentanediol and sodium palmitoyl sarcosinate.

Particularly preferably the mixture according to the invention is not an oil-in-water emulsion and not a dispersion of a fatty phase in water.

The compounds of constituents (i), (ii) and (iii) of a mixture according to the invention are substances that are known per se, each of which is also commercially available.

A mixture according to the invention contains, as constituent (i), one or a plurality of 1,2-alkane diols with 5 through 8 carbon atoms. The 1,2-alkane diols with 5 through 8 carbon atoms are preferably unbranched, i.e. linear, alkane diols, i.e. 1,2-n-alkane diols. 1,2-Pentanediol (pentane-1,2-diol), 1,2-hexanediol and/or 1,2-octanediol are preferred. 1,2-Pentanediol and/or 1,2-hexanediol are more preferred, and 1,2-pentanediol is particularly preferred, as the best results in the sense of the present invention were achieved in particular with 1,2-pentanediol (CAS number 5343-92-0; INCI: pentylene glycol).

A mixture according to the invention contains, as constituent (ii), one or a plurality of ammonium-, sodium- or potassium-$R^{alk}$-sarcosinates, wherein the structural element $R^{alk}$ represents alkanoyl, alkenoyl or alkadienoyl with 12 through 22 carbon atoms. The compounds of constituent (ii) are the Na or K salts of N-alkanoyl-N-methylglycine, N-alkenoyl-N-methylglycine or N-alkadienoyl-N-methylglycine, corresponding to the IUPAC nomenclature ammonium-, sodium- or potassium-2-[alkanoyl(methyl)amino]acetates, ammonium-, sodium- or potassium-2-[alkenoyl(methyl)amino]acetates or ammonium-, sodium- or potassium-2-[alkadienoyl(methyl)amino]acetates.

The compounds of constituent (ii) can be regarded as reaction products of sarcosine (N-methylglycine) with alkane-carboxylic acids, alkene-carboxylic acids or alkadiene-carboxylic acids with 12 through 22 carbon atoms and can be described by the following structural formula:

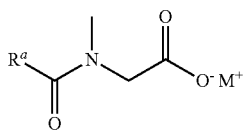

wherein $R^a$ is an alkyl residue, an alkenyl residue or an alkadienyl residue with 11 through 21 carbon atoms and $M^+$ represents ammonium ($NH_4^+$ ion), sodium ($Na^+$ ion) or potassium ($K^+$ ion). $R^a$ can therefore have no, one or two C—C double bonds.

As examples of compounds of constituent (ii), we may mention sodium lauroyl sarcosinate (CAS number 137-16-6), sodium myristoyl sarcosinate, potassium palmitoyl sarcosinate, sodium stearoyl sarcosinate, sodium oleoyl sarcosinate, potassium oleoyl sarcosinate, sodium linoleoyl sarcosinate, potassium lauroyl sarcosinate, potassium cocoyl sarcosinate, sodium cocoyl sarcosinate, ammonium lauroyl sarcosinate and ammonium cocoyl sarcosinate. Among these, the compounds of the group consisting of sodium lauroyl sarcosinate (CAS number 137-16-6), sodium myristoyl sarcosinate, potassium palmitoyl sarcosinate, sodium stearoyl sarcosinate, sodium oleoyl sarcosinate, potassium oleoyl sarcosinate and sodium linoleoyl sarcosinate are preferred.

Preferred are those ammonium-, sodium- or potassium-$R^{alk}$-sarcosinates used according to the invention, in which the structural element $R^{alk}$ represents alkanoyl, alkenoyl or alkadienoyl with 16 through 22 carbon atoms, more preferably with 16 through 20 carbon atoms, particularly preferably with 18 carbon atoms (correspondingly, $R^a$ in the structural formula shown above preferably represents an alkyl, alkenyl or alkadienyl residue with 15 through 19 carbon atoms, particularly preferably with 17 carbon atoms). Ammonium-, sodium- or potassium-$R^{alk}$-sarcosinates in which the structural element $R^{alk}$ represents alkenoyl, and preferably n-alkenoyl (correspondingly $R^a$=n-alkenyl in the above structural formula), are also preferred. Sodium oleoyl sarcosinate (CAS number 14351-62-3; INCI: sodium oleoyl sarcosinate) is further preferred, as excellent results in the sense of the present invention were achieved in particular with sodium oleoyl sarcosinate.

Herein the ammonium —$R^{alk}$-sarcosinates are in practice generally somewhat less preferred, in comparison to sodium- or potassium-$R^{alk}$-sarcosinates.

A mixture according to the invention contains, as optional constituent (iii), one or a plurality of sodium- or potassium-C10-C16-alkyl-sulfoacetates, i.e. sodium or potassium alkyl-sulfoacetates, in which the alkyl group has 10 through 16 carbon atoms.

The compounds of constituent (iii) can be described by the following structural formula:

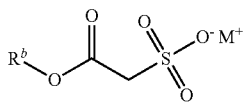

wherein $R^b$ is an alkyl residue with 10 through 16 carbon atoms and $M^+$ represents sodium ($Na^+$-Ion) or potassium ($K^+$ Ion).

The compounds of constituent (iii) can be regarded as sodium or potassium salts of the esterification products of sulfoacetic acid with 1-alkanols with 10 through 16 carbon atoms.

Those sodium- or potassium-C10-C16-alkyl-sulfoacetates used according to the invention, in which the alkyl group is unbranched (correspondingly $R^b$=n-alkyl in the above structural formula) are preferred. Sodium- or potassium-C10-C14-n-alkyl-sulfoacetates are further preferred, and in particular sodium or potassium lauryl sulfoacetate and sodium or potassium myristyl sulfoacetate. Sodium lauryl sulfoacetate (CAS number 1847-58-1; INCI: sodium lauryl sulfoacetate) is particularly preferred, as further-improved results in the sense of the present invention were achieved in particular when using sodium lauryl sulfoacetate together with the constituents (i) and (ii).

Preferred mixtures according to the invention are those that comprise constituents that are characterized as preferred or particularly preferred, preferably in one of the embodiments characterized above or in the following as preferred or particularly preferred, as particularly good results in the sense of the present invention were achieved with these.

A mixture comprising (i) 1,2-pentanediol and (ii) sodium oleoyl sarcosinate and optionally (iii) sodium lauryl sulfoacetate is particularly preferred according to the invention.

It was found, surprisingly, that (a) one or a plurality of 1,2-alkane diols with 5 through 8 carbon atoms can be used in combination with (b) one or a plurality of compounds from the group consisting of ammonium-, sodium- or potassium-$R^{alk}$-sarcosinates, wherein the structural element $R^{alk}$ represents alkanoyl, alkenoyl or alkadienoyl with 12 through 22 carbon atoms, preferably with 16 through 22 carbon atoms, sodium- or potassium-C10-C16-alkyl-sulfoacetates and mixture thereof (i.e. a mixture of (a) and (b))

as solubilizer for one or a plurality of organic substances,
for increasing the solubility of one or a plurality of organic substances,
for decreasing the turbidity of a preparation, preferably a dispersion and/or emulsion, containing one or a plurality of organic substances, and/or
for increasing the transparency of a preparation, preferably a dispersion and/or emulsion, containing one or a plurality of organic substances, wherein the organic substances preferably have in each case a log $K_{OW}$ value in the range from 1 through 12, preferably in the range from 2 through 10, particularly preferably in the range from 3 through 8.

It will be understood that these organic substances are additional organic substances, which do not satisfy the respective definitions of the constituents (i), (ii) or (iii) of a mixture according to the invention. These organic substances therefore cannot be assigned to any of the constituents (i), (ii) or (iii) of a mixture according to the invention.

A use that is preferred according to the invention is characterized in that one or a plurality of organic substances have a log $K_{OW}$ value in the range from 1 through 12, preferably in the range from 2 through 10, particularly preferably in the range from 3 through 8, and is or are selected from the group of substances suitable for use in cosmetic preparations, preferably in body care products.

Preferred groups of substances, which have corresponding log $K_{OW}$ values and are suitable for use in cosmetic preparations, in particular in body care products, are perfume oils, odoriferous substances, essential oils, active substances, antioxidants, substances with a cooling action, substances with a deodorant action, UV filters, vitamins, substances with a skin lightening action and anti-irritant active substances.

The log-$K_{OW}$ value denotes the octanol-water distribution coefficient. In the context of the present text, the term "log-$K_{OW}$ value" denotes the value calculated on the basis of the respective molecular structure using the software program "EPI Suite™ v4.00" of the United States Environmental Protection Agency, Washington D.C., USA, which in its turn uses the software program "KOWWIN™", which operates according to the atom/fragment contribution method.

The mixtures according to the invention are liquid and clear at 25° C. and 1013 mbar and preferably are characterized, in particular in the embodiments characterized as preferable, by cold cloud points below +10° C.

Mixtures according to the invention are transparent and have in particular a turbidity of less than 3 NTU (nephelometric turbidity units) according to DIN ISO EN 27027.

Moreover, the mixtures according to the invention are only slightly colored, as a rule transparent light yellow. In addition the mixtures according to the invention do not have an unpleasant odor and only display a faint intrinsic odor.

The mixtures according to the invention have, with respect to color and odor, improved properties compared with solubilizers usual up to now.

In a mixture according to the invention, the weight ratio of constituent (i), preferably 1,2-pentanediol, to constituent (ii), preferably sodium oleoyl sarcosinate, is in the range from 5:1 through 1:5, preferably in the range from 3:1 through 1:3, preferably in the range from 2:1 through 1:2, more preferably in the range from 3:2 through 2:3, particularly preferably in the range from 4:3 through 3:4, quite particularly preferably in the range from 8:7 through 7:8.

A mixture according to the invention can be used, even at low dosage, for the production of stable preparations, in particular of stable aqueous cosmetic preparations.

A mixture according to the invention or a composition according to the invention (as defined hereunder) is preferably free from polyethylene glycol (PEG).

In our own investigations it was found, among other things, that mixtures comprising 1,2-pentanediol, sodium oleoyl sarcosinate and sodium lauryl sulfoacetate have further-improved solubilizing properties compared with mixtures that only comprise 1,2-pentanediol and sodium oleoyl sarcosinate or only pentane-1,2-diol and sodium lauryl sulfoacetate.

However, if instead of 1,2-pentanediol another organic di- or triol was used, such as for example propylene glycol or glycerol, poorer results were achieved. Thus, the mixtures investigated, comprising propylene glycol, sodium oleoyl sarcosinate and sodium lauryl sulfoacetate or glycerol, sodium oleoyl sarcosinate and sodium lauryl sulfoacetate were in each case not clear and moreover still contained undissolved solids (in this connection, see also example 1 given below).

Moreover, it was found that constituent (i), here in particular 1,2-pentanediol, compared with various other glycols such as 1,2-propylene glycol or compared with glycerol, enhances the solubilizing properties of constituent (ii), here in particular sodium oleoyl sarcosinate, or of constituent (iii), here in particular sodium lauryl sulfoacetate, or mixtures of the constituents (ii) and (iii), far more and as a result markedly better properties were achieved.

Therefore mixtures according to the invention are preferred that comprise the constituents (i), (ii) and (iii), here preferably pentane-1,2-diol, sodium oleoyl sarcosinate and sodium lauryl sulfoacetate, preferably in one of the embodiments characterized above or hereunder as preferable or particularly preferable, because particularly good results in the sense of the present invention were achieved with these mixtures.

A mixture according to the invention preferably comprises:
    5 through 30 wt. %, preferably 10 through 20 wt. %, preferably 12 through 18 wt. %, particularly preferably 13 through 17 wt. % of constituent (i), and preferably pentane-1,2-diol,
    5 through 30 wt. %, preferably 10 through 20 wt. %, preferably 12 through 18 wt. %, particularly preferably 13 through 17 wt. % of constituent (ii), and preferably sodium oleoyl sarcosinate,
    optionally 3 through 22 wt. %, preferably 5 through 20 wt. %, preferably 8 through 20 wt. %, particularly preferably 11 through 17 wt. % of constituent (iii), and preferably sodium lauryl sulfoacetate,
wherein the percentages by weight refer in each case to the total mass of the mixture.

A preferred mixture according to the invention comprises or consists of:
    10 through 20 wt. %, preferably 12 through 18 wt. %, preferably 13 through 17 wt. %, particularly preferably 14 through 16 wt. % of constituent (i), and preferably pentane-1,2-diol,
    10 through 20 wt. %, preferably 12 through 18 wt. %, preferably 13 through 17 wt. %, particularly preferably 13 through 16 wt. % of constituent (ii), and preferably sodium oleoyl sarcosinate,
    5 through 20 wt. %, preferably 8 through 20 wt. %, preferably 11 through 17 wt. %, particularly preferably 12 through 16.5 wt. % of constituent (iii), and preferably sodium lauryl sulfoacetate,
    25 wt. % or more of water, preferably 30 through 60 wt. % water, preferably 35 through 55 wt. % water,
    optionally sodium oleate, preferably 0.5 through 5 wt. % of sodium oleate, preferably 1 through 3 wt. %,
    optionally sodium chloride, preferably 1 through 5 wt. % of sodium chloride, preferably 1.5 through 4 wt. %,
    optionally disodium sulfoacetate, preferably 0.5 through 3 wt. %, preferably 0.6 through 2 wt. %,
    optionally sodium sulfate, preferably 0.5 through 3 wt. %, preferably 1 through 2 wt. %,
wherein the percentages by weight refer in each case to the total mass of the mixture.

A particularly preferred mixture according to the invention comprises or consists of:
    12 through 18 wt. %, preferably 13 through 17 wt. %, preferably 14 through 16 wt. % of constituent (i), and preferably pentane-1,2-diol,
    12 through 18 wt. %, preferably 13 through 17 wt. %, preferably 13 through 16 wt. % of constituent (ii), and preferably sodium oleoyl sarcosinate,
    8 through 20 wt. %, preferably 8 through 18 wt. %, preferably 11 through 17 wt. %, more preferably 12 through 16.5 wt. % of constituent (iii), and preferably sodium lauryl sulfoacetate,
    30 wt. % or more of water, preferably 30 through 60 wt. % water, preferably 35 through 55 wt. % water,
    optionally sodium oleate, preferably 0.5 through 5 wt. % of sodium oleate, preferably 1 through 3 wt. %,
    sodium chloride, preferably 1 through 5 wt. % of sodium chloride, preferably 1.5 through 4 wt. %,
    disodium sulfoacetate, preferably 0.5 through 3 wt. %, preferably 0.6 through 2 wt. %,
    sodium sulfate, preferably 0.5 through 3 wt. %, preferably 1 through 2 wt. %,
wherein the percentages by weight refer in each case to the total mass of the mixture.

Owing to the chemical composition of the mixtures according to the invention, their physical and chemical properties are largely determined, but certain variations are nevertheless possible.

In a preferred embodiment a mixture according to the invention has a pH value of 6 or higher, preferably a pH value of 6.5 or higher.

The pH value of a mixture according to the invention is preferably in the range from 6 through 7.5.

It was found that said mixtures according to the invention have a further improved dissolving power and even better solubilizing properties, in particular in comparison with mixtures with a pH value of less than 6.

The pH value of a mixture according to the invention can be adjusted for example by adding a base, preferably an inorganic base for example alkali metal hydroxides or alkaline-earth metal hydroxides, and preferably NaOH or KOH, wherein the inorganic base is preferably added as aqueous solution.

In another aspect the present invention relates to a composition for producing a cosmetic preparation, preferably a body care product, comprising a mixture according to the invention, preferably in one of the aforementioned preferred embodiments, and one or a plurality of organic substances with a log $K_{OW}$ value (as defined above) in the range from 1 through 12, preferably in the range from 2 through 10, particularly preferably in the range from 3 through 8.

The mixtures according to the invention permit the production of transparent compositions and transparent cosmetic preparations, wherein said compositions or preparations have excellent storage stability, preferably over a period of 3 months, in particular over a period of 6 months.

The storage stability of the mixtures and compositions according to the invention was characterized in that no demixing or phase separation was observed during the storage time of 3 or preferably 6 months in daylight and at constant storage temperature, preferably at a constant storage temperature of 50° C., preferably at a constant storage temperature of 40° C., preferably at a constant storage temperature of 25° C., in particular preferably at a constant storage temperature of 5° C.

In addition, mixtures and compositions according to the invention have good stability, i.e. no, no substantial or, only in exceptional cases, slight, insignificant changes were observed in the aforementioned storage conditions and times with respect to viscosity, pH value, color and odor.

Preferably a composition according to the invention has very little turbidity. The turbidity is measured in NTU (nephelometric turbidity units).

A composition that is preferred according to the invention is transparent, and preferably has a turbidity of less than 10 NTU, preferably of less than 5 NTU, particularly preferably of less than 3 NTU, in each case determined according to DIN ISO EN 27027.

The turbidity in the context of the present invention is measured according to DIN ISO EN 27027 with 90° IR scattered light.

The turbidity can be measured for example with a Hach 2100N IS laboratory nephelometer with 860 nm (infrared) LED or with a laboratory turbidity photometer NEPHLA from Dr. Bruno Lange GmbH & Co. KG.

The storage stability of a transparent composition according to the invention was characterized in that during a storage time of 3 or preferably 6 months in daylight and at constant storage temperature it remained transparent, preferably at a constant storage temperature of 50° C., preferably at a constant storage temperature of 40° C., preferably at a constant storage temperature of 25° C., in particular preferably at a constant storage temperature of 5° C.

A composition that is further preferred according to the invention is characterized in that the total amount of organic substance(s) with a log $K_{OW}$ value in the range from 1 through 12 is in the range from 0.1 through 5 wt. %, preferably in the range from 0.1 through 3 wt. %, preferably in the range from 0.15 through 1 wt. %, particularly preferably in the range from 0.2 through 0.8 wt. %, in each case relative to the total mass of the composition.

Herein, preferred organic substance(s) preferably have a log $K_{OW}$ value in the range from 2 through 10, particularly preferably in the range from 3 through 8, and are preferably selected from the group of substances suitable for use in cosmetic preparations, preferably in body care products. Said preferred groups of substances, which have corresponding log $K_{OW}$ values, are perfume oils, odoriferous substances, essential oils, active substances, antioxidants, substances with a cooling action, substances with a deodorant action, UV filters, vitamins, substances with a skin lightening action and anti-irritant active substances.

In our own investigations, the following substances were used as representative organic substances, from the group of substances with a cooling action, excipients, essential oils and perfume oils etc.:

Frescolat® ML (menthyl lactate), sage oil (*Salvia officinalis* oil), avocado oil (*Persea gratissima* oil), almond oil (*Prunus amygdalus dulcis* oil), rose oil (*Rosa Damascena* Flower Oil), various perfume oils (with the names Lait de Rose, Lait Vitamine Sun, L'Eau d'été, Jasmin Flowers), bisabolol, farnesol, Crinipan® AD (climbazole anti-dandruff agent), cetearyl ethylhexanoate, paraffin oil (paraffinum liquidum) and Dragocid® Liquid (preservative mixture of phenoxyethanol, methylparaben, ethylparaben, butylparaben, propylparaben and isobutylparaben).

A composition that is further preferred according to the invention is characterized in that the weight ratio of the total amount of constituent (i), and preferably pentane-1,2-diol, and constituent (ii), and preferably sodium oleoyl sarcosinate, to the total amount of substances with a log $K_{OW}$ value in the range from 1 through 12 is greater than 0.5, preferably greater than 0.75, preferably greater than 1, particularly preferably greater than 1.25.

A composition according to the invention is characterized by, among other things:
good viscosity stability,
good pH-stability,
good temperature stability,
good color stability,
good odor stability.

In another aspect the invention relates to a cosmetic preparation, preferably a body care product, comprising
   a mixture according to the invention, preferably in one of the embodiments characterized as preferable, and one or a plurality of organic substances with a log $K_{OW}$ value in the range from 1 through 12, preferably in the range from 2 through 10, particularly preferably in the range from 3 through 8
   or
   a composition according to the invention, preferably in one of the embodiments characterized as preferable
and
   optionally further cosmetically effective constituents, preferably constituents that are effective for body care,
   optionally other constituents.

Cosmetic preparations according to the invention are preferably transparent and have in particular a turbidity of less than 10 NTU (nephelometric turbidity units) according to DIN ISO EN 27027.

Moreover, a mixture according to the invention, a composition according to the invention or a cosmetic preparation according to the invention provides very good skin moisturizing action, and thus also counteracts drying of the skin.

Substances and excipients that a composition according to the invention or cosmetic preparation containing a mixture according to the invention can additionally contain are for example:

Preservatives, preferably those mentioned in US 2006/0089413, abrasives, anti-acne agents and sebum reducing agents, preferably those mentioned in WO 2008/046791, agents against skin ageing, preferably those mentioned in WO 2005/123101, antibacterial agents, anticellulitis agents, anti-dandruff agents, preferably those mentioned in WO 2008/046795, anti-inflammatory agents, irritation-preventing agents, anti-irritants (anti-inflammatory, irritation-inhibiting and irritation-preventing agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carriers, preferably those mentioned in WO 2005/123101, chelating agents, preferably those mentioned in WO 2005/123101, cell stimulants, cleansers, care agents, depilatories, surface active substances, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film-forming agents, fixatives, foaming agents, foam stabilizers, anti-foaming agents, foam boosters, fungicides, gelling agents and gel-forming agents, preferably those mentioned in WO 2005/123101, hair care products, hair shaping agents, hair straightening agents, moisture regulators (hydrating, moistening and/or moisturizing substances), preferably those mentioned in WO 2005/123101, osmolytes, preferably those mentioned in WO 2005/123101, compatible solutes, preferably those mentioned in WO 01/76572 and WO 02/15686, bleaching agents, tonics, stain removers, optical brighteners, impregnating agents, dirt-repellent agents, friction-reducing agents, lubricants, plasticizers, opacifiers, gloss agents, polymers, preferably those mentioned in WO 2008/046676, powders, proteins and protein hydrolysates, preferably those mentioned in WO 2005/123101 and WO 2008/046676, refatting agents, abrading agents, skin calmatives, skin cleansers, skin care agents, skin repair agents, preferably containing cholesterol and/or fatty acids and/or ceramides and/or pseudoceramides, and preferably those mentioned in WO 2006/053912, skin lightening agents, preferably those mentioned in WO 2007/110415, skin protectants, skin-softening agents, skin cooling agents, preferably those mentioned in WO 2005/123101, skin warming agents, preferably those mentioned in WO 2005/123101, stabilizers, UV absorbents and UV filters, preferably those mentioned in WO 2005/123101, benzylidene-beta-dicarbonyl compounds, preferably those mentioned in WO 2005/107692, alpha-benzoylcinnamic acid nitriles, preferably those mentioned in WO 2006/015954, AhR-receptor antagonists, preferably those mentioned in WO 2007/128723 and WO 2007/060256, detergents, fabric softeners, suspending agents, tanning agents, preferably those mentioned in WO 2006/045760, thickeners, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, mono- or polyunsaturated fatty acids, α-hydroxy acids, polyhydroxy fatty acids), preferably those mentioned in WO 2005/123101, liquefiers, dyes and color protectants and pigments, preferably those mentioned in WO 2005/123101, anticorrosive agents, aromas, flavorings and odoriferous substances, preferably those listed in S. Arctander, Perfume and Flavor Chemicals, self-published, Montclair, N.J., 1969 and Surburg, Panten, Common Fragrance and Flavor Materials, 5th edition, Wiley-VCH, Weinheim 2006, in particular those explicitly mentioned in US 2008/0070825, alcohols and (other) polyols, preferably those mentioned in WO 2005/123101, other surfactants, preferably those mentioned in WO 2005/123101, animal extracts, yeast extracts, extracts from algae or microalgae, electrolytes, liquefiers, organic solvents, preferably those mentioned in WO 2005/123101, or silicones and silicone derivatives, preferably those mentioned in WO 2008/046676.

Preferred liquid carriers, which can be a constituent of a cosmetic preparation according to the invention, are selected from the group consisting of glycerol, 1,2-propylene glycol, 1,2-butylene glycol, 1,3-butylene glycol, 1,2-decanediol and ethanol and mixtures of two or a plurality of the aforementioned liquid carriers.

The proportion of liquid carriers can vary considerably depending on the respective product type of a cosmetic preparation according to the invention. The total amount of glycerol, 1,2-propylene glycol, 1,2-butylene glycol and ethanol is preferably in the range from 1 through 50 wt. %, preferably in the range from 3 through 40 wt. %, relative to the total weight of the preparation according to the invention.

Preferably the total amount of water in a cosmetic preparation according to the invention is in the range from 20 through 90 wt. %, preferably in the range from 30 through 85 wt. %, more preferably in the range from 40 through 80 wt. %, relative to the total weight of the preparation.

Furthermore, additionally for improvement of skin moisture and/or due to the preserving properties, the alcohols of constituent (i), in particular pentane-1,2-diol, in, can be contained in a total amount of up to 10 wt. % in cosmetic preparations according to the invention. This amount is understood as including the amount of constituent (i) that is incorporated in a cosmetic preparation according to the invention, as a constituent of a mixture or composition according to the invention.

Preferred solid carriers that can be a constituent of a preparation according to the invention are hydrocolloids such as starches, degraded starches, chemically or physically modified starches, dextrins, (powdered) maltodextrins (preferably with a dextrose-equivalent value of 5 through 25, preferably 10-20), lactose, silica, glucose, modified celluloses, gum arabic, ghatti gum, tragacanth, karaya, carrageenan, pullulan, curdlan, xanthan gum, gellan gum, guar flour, carob flour, alginates, agar, pectin and inulin and mixtures of two or a plurality of these solids, in particular maltodextrins (preferably with a dextrose-equivalent value of 15-20), lactose, silica and/or glucose.

The amounts of cosmetic excipients and carriers to be used in each case can easily be determined by a person skilled in the art in relation to the type of the particular cosmetic preparation.

Preparations according to the invention preferably contain one or a plurality of preservatives or one or a plurality of antioxidants.

The amount of antioxidants (one or a plurality of compounds) in the preparations is preferably 0.001-10 wt. %, particularly preferably 0.05-5 wt. %, in particular 0.1-3 wt. %, relative to the total weight of the preparation.

Advantageously, the antioxidants are selected from the following group: amino acids (e.g. glycine, histidine, 3,4-dihydroxyphenylalanine, tyrosine, tryptophan) and derivatives thereof, imidazoles (e.g. urocaninic acid) and derivatives thereof, peptides (D,L-carnosine, D-carnosine, L-carnosine, anserine) and derivatives thereof, carotenoids, carotenes (e.g. alpha-carotene, beta-carotene, lycopene) and derivatives thereof, chlorogenic acid and derivatives thereof, lipoic acid and derivatives thereof, aurothioglucose, propylthiouracil and other thiols (e.g. thioredoxin, glutathione, cysteine, cystine, cystamine and glycosyl- and N-acyl derivatives thereof or alkyl esters thereof) and salts thereof, dilauryl thiodipropionate, distearyl thiodipropionate, thiodipropionic acid and derivatives thereof and phenylic carboxylic acid amides of phenolic benzylamines (e.g. homovanillic acid amides, 3,4-d ihydroxyphenylacetic acid amides, ferulic acid amides, sinapic acid amides, caffeic acid amides, dihydroferulic acid amides, dihydrocaffeic acid amides, vanillomandelic acid amides or 3,4-dihydroxymandelic acid amides of 3,4-dihydroxybenzyl, 2,3,4-trihydroxybenzyl or 3,4,5-trihydroxybenzyl amine), catecholoximes or catecholoxime ethers (e.g. 3,4-dihydroxybenzaldoxime or 3,4-dihydroxybenzaldehyde-O-ethyloxime), 2-hydrazino-1,3-thiazoles and derivatives thereof, also (metal-) chelating agents (e.g. 2-hydroxy fatty acids, phytic acid, lactoferrin), humic acid, bile acids, bile extracts, bilirubin, biliverdin, folic acid and derivatives thereof, ubiquinone and ubiquinol and derivatives thereof, vitamin C and derivatives thereof (e.g. ascorbyl palmitate, magnesium ascorbyl phosphate, ascorbyl acetate), tocopherols and derivatives (e.g. vitamin-E acetate), vitamin A and derivatives (e.g. vitamin-A palmitate), rutinic acid and derivatives thereof, flavonoids (e.g. quercetin, alpha-glucosyl rutin) and derivatives thereof, phenylic carboxylic acids (e.g. gallic acid, ferulic acid) and derivatives thereof (e.g. gallic acid propyl ester, ethyl ester, octyl ester), furfurylidene glucitol, dibutyl hydroxytoluene, butyl hydroxyanisole, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, resveratrol).

If vitamin E or vitamin E derivatives are used as antioxidants, their total concentration is preferably in the range 0.01-5 wt. %, preferably in the range 0.1-3 wt. %, relative to the total weight of the cosmetic preparation according to the invention.

If vitamin A or vitamin A derivatives, or carotenes or their derivatives are used as antioxidants, their total concentration is preferably in the range 0.01-5 wt. %, preferably in the range 0.1-3 wt. %, relative to the total weight of the cosmetic preparation according to the invention.

The one or a plurality of further substances with physiological cooling action, which can be used as constituents in a composition according to the invention or a cosmetic preparation according to the invention, are preferably selected from the following list: menthol and menthol derivatives (e.g. L-menthol, D-menthol, racemic menthol, isomenthol, neoisomenthol, neomenthol) menthyl ethers (e.g. (I-menthoxy)-1,2-propanediol, (I-menthoxy)-2-methyl-1,2-propanediol, 1-menthyl-methyl ether), menthyl esters (e.g. menthyl formate, menthyl acetate, menthyl isobutyrate, menthyl lactates, L-menthyl-L-lactate, L-menthyl-D-lactate, menthyl-(2-methoxy)acetate, menthyl-(2-methoxyethoxy)acetate, menthyl pyroglutamates), menthyl carbonates (e.g. menthyl propylene glycol carbonate, menthyl ethylene glycol carbonate, menthyl glycerol carbonate or mixtures thereof), the semi-esters of menthols with a dicarboxylic acid or derivatives thereof (e.g. mono-menthyl succinate, mono-menthyl glutarate, mono-menthyl malonate, O-menthyl succinic acid ester-N,N-(dimethyl) amide, O-menthyl succinic acid ester amide), menthanecarboxylic acid amides (and preferably menthane-carboxylic acid-N-ethyl amide [WS3] or $N^\alpha$-(menthane-carbonyl) glycine ethyl ester [WS5], as described in U.S. Pat. No. 4,150,052, menthane-carboxylic acid-N-(4-cyanophenyl) amide or menthane-carboxylic acid-N-(4-cyanomethylphenyl)amide as described in WO 2005/049553, menthane-carboxylic acid-N-(alkoxyalkyl)amides), menthone and menthone derivatives (e.g. L-menthone glycerol ketal), 2,3-dimethyl-2-(2-propyl)-butanoic acid derivatives (e.g. 2,3-dimethyl-2-(2-propyl)-butanoic acid-N-methylamide [WS23]), isopulegol or its esters (I-(−)-isopulegol, I-(−)-isopulegol acetate), menthane derivatives (e.g. p-menthane-3,8-diol) or cubebol.

In a preferred embodiment, a cosmetic preparation according to the invention contains at least one UVA filter and/or at least one UVB filter and/or at least one inorganic pigment. The preparations can then be in various forms, such as are for example usually employed for sunscreen preparations. They can for example form a solution, an emulsion of the water-in-oil (W/O) type or of the oil-in-water (O/W) type, or a multiple emulsion, e.g. of the water-in-oil-in-water (W/O/W) type, a gel, a hydrodispersion, a solid stick or also a spray.

Preparations according to the invention in the area of cosmetics, which contain a mixture according to the invention or a composition according to the invention (in each case as defined above), are especially advantageously combined with substances that absorb or reflect UV radiation, particularly for cosmetic or skin-protecting purposes, wherein the total amount of the filtering substances is from 0.01 through 30 wt. %, preferably 0.1 through 20 wt. %, in particular 1 through 15 wt. %, relative to the total weight of the preparations, in order to provide cosmetic preparations that protect the hair or the skin against ultraviolet radiation. Advantageously, the cosmetic preparations according to the invention contain at least one UVA filter and/or at least one UVB filter and/or at least one inorganic pigment, so that a sun protection factor of at least >2 (preferably >5) is attained.

Advantageous inorganic sunscreen pigments are finely-divided metal oxides and metal salts which are also mentioned in WO 2005/123101. The total amount of inorganic pigments, in particular hydrophobic inorganic micropigments in a cosmetic preparation according to the invention is preferably in the range from 0.1 through 20 wt. %, more preferably in the range from 0.5 through 15 wt. %, relative to the total weight of the preparation.

A combination of the mixtures or compositions with UV filters (UV/A, UV/B and wide-band filters) according to the invention (sunscreen agents) is particularly advantageous. The use of the mixtures according to the invention has co-emulsifying properties and regularly leads to an improvement of storage stability, an increase of the UVA and/or UVB sun protection factors (SPF) and of the waterproofness of corresponding sunscreen products.

In a preferred embodiment, a mixture or composition according to the invention is formulated together with sunscreen agents. Preferred sunscreen agents are e.g. organic UV absorbers from the class of 4-aminobenzoic acid and derivatives, salicylic acid derivatives, benzophenone derivatives, dibenzoylmethane derivatives, diphenyl acrylates, 3-imidazol-4-yl-acrylic acid and esters thereof, benzofuran derivatives, benzylidene malonate derivatives, polymeric UV absorbers (containing one or a plurality of organosilicon residues), cinnamic acid derivatives, camphor derivatives, trianilino-s-triazine derivatives, 2-hydroxyphenylbenzotriazole derivatives, 2-phenylbenzimidazole-5-sulfonic acid and salts thereof, anthranilic acid menthyl ester, benzotriazole derivatives.

The total amount of all water-soluble UV filtering substances in a preferred cosmetic preparation according to the invention is preferably in the range from 0.1 through 12 wt. %, preferably 0.5 through 8 wt. %, relative to the total weight of the preparation according to the invention.

Those that are preferred are (mono- or poly-) sulfonated water-soluble UV filters, which are preferably selected from the group consisting of phenylene-bis-benzimidazyl-tetrasulfonic acid disodium salt or salts thereof and/or the corresponding disulfonic acid or salts thereof and/or 2-phenylbenzimidazole-5-sulfonic acid or salts thereof and/or 2-hydroxy-4-methoxybenzophenone-5-sulfonic acid or salts thereof and/or 4-(2-oxo-3-bornylidene-methyl)-benzene sulfonic acid or salts thereof and/or 2-methyl-5-(2-oxo-3-bornylidene-methyl)-benzene sulfonic acid or salts thereof and/or benzene-1,4-di-(2-oxo-3-bornylidene-methyl)-10-sulfonic acid or salts thereof.

Advantageous UV filters and inorganic sunscreen pigments are mentioned in WO 2005/123101. UV absorbers particularly suitable for combination are also mentioned in WO 2005/123101.

Particularly suitable UV filters are
p-aminobenzoic acid
3-(4'-trimethylammonium)-benzylidene-bornan-2-one-methylsulfate
salicylic acid-homomenthyl ester (Neo Heliopan HMS)
2-hydroxy-4-methoxy-benzophenone (Neo Heliopan BB)
2-phenylbenzimidazole sulfonic acid (Neo Heliopan Hydro)
terephthalylidene-dibornanesulfonic acid and salts (Mexoryl® SX)
4-tert.-butyl-4'-methoxydibenzoylmethane (Neo Heliopan 357)
3-(4'-sulfo)benzylidene-bornan-2-one and salts
2-ethylhexyl-2-cyano-3,3-diphenyl acrylate (Neo Heliopan 303)
N-[(2 and 4)-[2-(oxoborn-3-ylidene)methyl]benzyl]-acrylamide polymer
p-methoxycinnamic acid-2-ethylhexyl ester (Neo Heliopan AV)
p-aminobenzoic acid-ethyl ester (25 mol) ethoxylated
p-methoxycinnamic acid-isoamyl ester (Neo Heliopan E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)-oxy)-disiloxanyl)-propyl) (Mexoryl®XL)
4,4'-[(6-[4-(1,1-dimethyl)-aminocarbonyl)-phenylamino]-1,3,5-triazine-2,4-diyl)-diimino]-bis(benzoic acid-2-ethylhexyl ester) (Uvasorb HEB)
3-(4'-methylbenzylidene)-d,l-camphor (Neo Helipan MBC)
3-benzylidene camphor
salicylic acid-2-ethylhexyl ester (Neo Helipan OS)
4-dimethylaminobenzoic acid-2-ethylhexyl ester (Padimate 0)
hydroxy-4-methoxy-benzophenone-5-sulfonic acid and Na-salt
2,2'-methylene-bis(6-(2H-benztriazol-2-yl)-4-1,1,3,3-tetramethylbutyl)-phenol) (Tinosorb®M)
phenylene-bis-benzimidazyl-tetrasulfonic acid disodium salt (Neo Heliopan AP)
2,4-bis-[{(4-(2-ethyl-hexyloxy)-2-hydroxyl}-phenyl]-6-(4-methoxyphenyl)-1,3,5-triazine (Tinosorb®S)
benzylidene malonate-polysiloxane (Parsol SLX)
menthyl anthranilate (Neo Heliopan MA)
2-(4-diethylamino-2-hydroxybenzoyl)-benzoic acid-hexyl ester (Uvinul® A Plus)
indanylidene compounds according to WO 02/38537

A mixture or composition according to the invention can furthermore be incorporated in cosmetic and/or dermatological preparations that contain pigments, preferably finely-divided pigments. These can be organic or inorganic pigments. A preferred organic pigment is 2,2'-methylene-bis-[6-(2H-benzotriazol-2-yl)-4-(1,1,3,3-tetramethylbutyl)-phenol] (Tinosorb® M). Suitable inorganic pigments or micropigments based on metal oxides and/or other metal compounds sparingly soluble or insoluble in water are in particular oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and blends of said oxides. These pigments are X-ray amorphous or non-X-ray amorphous. Finely-divided pigments based on $TiO_2$ and ZnO are particularly preferred.

In many embodiments, cosmetic preparations according to the invention contain one or a plurality of (metal)-chelating agents. (Metal)-chelating agents whose use is preferred are the compounds mentioned in WO 2005/123101.

The amount of anti-irritants (one or a plurality of compounds) in a cosmetic preparation according to the invention is preferably 0.0001-10 wt. %, in particular 0.001-5 wt. %, relative to the total weight of the preparation.

A mixture according to the invention or a composition according to the invention (in each case as defined above) can, in particular in cosmetic preparations according to the invention, advantageously be used in combination with insect repellents, e.g. DEET, IR 3225 or Drago-Repel-X™ (Symrise).

A mixture according to the invention or a composition according to the invention (in each case as defined above) can, in particular in cosmetic preparations according to the invention, advantageously be used in combination with hair care products and anti-dandruff agents (e.g. climbazole, ketoconazole, piroctone olamine, zinc-pyrithione).

A mixture according to the invention or a composition according to the invention (in each case as defined above) can in a great many cases also be used advantageously in combination with one or a plurality of preservatives in preparations according to the invention. The preservatives mentioned in WO 2005/123101 are preferably selected.

Cosmetic preparations according to the invention can also contain plant extracts that are usable for cosmetic purposes. The plant extracts are preferably selected from the substances listed in the table beginning on page 44 of the 3rd edition of the manual on declaration of ingredients of cosmetics, issued by the Industrieverband Körperpflegemittel and Waschmittel e.V. (IKW; "industrial association for body care products and detergents"), Frankfurt. Moreover, in particular the extracts mentioned in WO 2005/123101 are advantageous.

Cosmetic preparations according to the invention can, in particular when crystalline or microcrystalline solids such as inorganic micropigments are to be incorporated in the preparations, additionally also contain anionic, cationic, non-ionic and/or amphoteric surfactants mentioned in WO 2005/123101.

As further stabilizers, cosmetic preparations according to the invention can additionally contain hydrogel forming agents, e.g. carbomers, acrylate-crosspolymers, xanthans, alginates etc.

The lipid phase can preferably comprise one or a plurality of substances, selected from the following groups of substances:
- mineral oils, mineral waxes,
- oils, such as triglycerides of decanoic or octanoic acid, other natural oils e.g. castor oil,
- fats, waxes and other natural and synthetic fats, preferably esters of fatty acids with alcohols with low number of carbons (<10), e.g. with isopropanol, propylene glycol or glycerol, or esters of fatty alcohols with alkanoic acids with low number of carbons (<10) or with fatty acids,
- alkylbenzoates,
- silicone oils and siloxanes, and preferably dimethylpolysiloxane, diethylpolysiloxane, diphenylpolysiloxane and mixtures thereof, cyclomethicone (octamethylcyclotetrasiloxane), hexamethylcyclotrisiloxane, polydimethylsiloxane and poly(methylphenylsiloxane).

The lipid phase of a cosmetic preparation according to the invention can preferably be selected from the group of esters from saturated and/or unsaturated, linear and/or branched alkane-carboxylic acids with a chain length from 3 through 30 carbon atoms and saturated and/or unsaturated, linear and/or branched alcohols with a chain length from 3 through 30 carbon atoms, from the group of esters from aromatic carboxylic acids and saturated and/or unsaturated, linear and/or branched alcohols with a chain length from 3 through 30 carbon atoms. Said ester oils can then advantageously be selected from the group isopropyl myristate, palmitate, stearate, oleate; n-butyl stearate, n-hexyllaurate, n-decyloleate, isooctyl stearate, isononyl stearate, isononylisononanate, 2-ethyl-hexylpalmitate, ethylhexyllaurate, 2-hexyldecyl stearate, 2-octyldodecylpalmitate, oleyl oleate, oleyl erucate, erucyl oleate and synthetic, semi-synthetic and natural mixtures of said esters, e.g. jojoba oil, 2-ethylhexyl-2-ethylhexanoate (e.g. Dragoxat EH), ethylhexyl isononanoate (e.g. Dragoxat 89), cetearyl-2-ethylhexanoate, diisopropyl adipate, triisononanoin.

Important areas of application for the mixtures and compositions according to the invention are cosmetic preparations, in particular aqueous cosmetic preparations, which (apart from the mixture according to the invention) are formulated as usual and serve for cosmetic light protection, for the treatment, care and cleaning of the skin and/or of the hair.

For application, the cosmetic preparations according to the invention are applied in the usual way for cosmetics in a sufficient amount on the skin and/or the hair.

Accordingly, depending on their structure, cosmetic preparations according to the invention can preferably be used as skin care products, e.g. skin protecting cream, day or night creams, sunscreen products, after-sun preparation (e.g. after-sun lotion) care mask, gel pads, face lotion, moist care and/or impregnating solution, e.g. for cosmetic wipes, cleaning wipes, cleaning soap, foam or shower gel, liquid soap, bar soap, shampoo (e.g. 2-in-1 shampoo, anti-dandruff shampoo, baby shampoo, shampoo for dry scalp, shampoo concentrate), hair care products, hair conditioners, hair coloring, hair rinse, hair styling products (e.g. hair gel), deodorants, antiperspirants (e.g. roll-on or stick), shaving preparations (e.g. aftershave balm, pre-shave or aftershave lotion) or as make-up remover.

A cosmetic preparation according to the invention is provided in the form of an emulsion, lotion, fluid, cream, micro-emulsion, gel (e.g. hydrogel or hydrodispersion gel), balsam, pump spray, alcoholic or aqueous/alcoholic solution.

In another aspect the invention relates to a cosmetic preparation, wherein the cosmetic preparation is a body care product, which is preferably selected from the group consisting of aqueous and aqueous-alcoholic systems such as shower gels, shampoos, alcoholic perfumes, aqueous-alcoholic perfumes, aftershave gels, creams, lotions, hair care products and hair styling products.

A cosmetic preparation preferred according to the invention is characterized in that the cosmetic preparation, preferably the body care product, comprises
  0.1 through 15 wt. %, preferably 0.5 through 7 wt. %, more preferably 0.5 through 5 wt. %, and particularly preferably 1 through 3 wt. % of a mixture according to the invention, preferably in one of the embodiments characterized as preferable,
or
  0.1 through 15 wt. %, preferably 0.5 through 7 wt. %, more preferably 0.5 through 5 wt. %, and particularly preferably 1 through 3 wt. % of a composition according to the invention, preferably in one of the embodiments characterized as preferable,
in each case relative to the total mass of the cosmetic preparation.

The amount of mixture according to the invention or composition according to the invention to be used in each case can easily be determined by a person skilled in the art depending on the nature of the particular cosmetic preparation, also depending on its application, its viscosity and the other active substances, auxiliaries and/or carriers present.

In another aspect the invention relates to a method of increasing the solubility of an organic substance and/or decreasing the turbidity of a preparation containing an organic substance and/or for increasing the transparency of a preparation containing one or a plurality of organic substances, wherein the organic substance in each case has a log $K_{OW}$ value in the range from 1 through 12, preferably in the range from 2 through 10, particularly preferably in the range from 3 through 8,
comprising the step:
  mixing the organic substance(s) with a mixture according to the invention, preferably in one of the embodiments characterized as preferable.

In another aspect the invention relates to a method of producing a mixture according to the invention, a composition according to the invention or a cosmetic preparation according to the invention, in each case preferably in one of the embodiments characterized as preferable, comprising the step:
  mixing of constituent (i) and constituent (ii) and optionally constituent (iii).

In a preferred embodiment, for producing a cosmetic preparation, the method according to the invention is carried out so that as a result of mixing, the organic substance(s) is/are dissolved in a mixture according to the invention, preferably resulting in a composition according to the invention in the form of a solution.

For the preferred organic substance(s), the foregoing applies correspondingly.

The present invention further relates to the use of a 1,2-alkane diol with 5 through 8 carbon atoms, and preferably of 1,2-pentanediol, or a mixture of 1,2-alkane diols with 5 through 8 carbon atoms, and preferably a mixture containing 1,2-pentanediol, for improving the solubilizing action, in particular the dissolving power, of surfactants.

The preferred surfactants are the compounds of constituents (ii) and/or (iii) of a mixture according to the invention that are characterized as preferable, and in particular sodium oleoyl sarcosinate, sodium lauryl sulfoacetate or mixture thereof, wherein a mixture of sodium oleoyl sarcosinate and sodium lauryl sulfoacetate in the weight ratio from 10:1 through 1:4, preferably in the weight ratio from 4:1 through 1:2, is further preferred.

EMBODIMENTS THAT ARE PARTICULARLY PREFERRED ACCORDING TO THE INVENTION

Embodiment 1

Use of pentane-1,2-diol in combination with a compound from the group consisting of sodium oleoyl sarcosinate and sodium lauryl sulfoacetate and mixture thereof
- as solubilizer for one or a plurality of organic substances,
- for increasing the solubility of one or a plurality of organic substances,
- for decreasing the turbidity of a preparation, preferably a dispersion and/or emulsion, containing one or a plurality of organic substances, and/or
- for increasing the transparency of a preparation, preferably a dispersion and/or emulsion, containing an organic substance, wherein the organic substance in each case preferably has a log $K_{OW}$ value in the range from 1 through 12, preferably in the range from 2 through 10, particularly preferably in the range from 3 through 8.

Embodiment 2

Use according to embodiment 1, characterized in that the organic substance has a log $K_{OW}$ value in the range from 1 through 12, preferably in the range from 2 through 10, particularly preferably in the range from 3 through 8, and is selected from the group of substances suitable for use in cosmetic preparations, preferably in body care products.

Embodiment 3

Mixture comprising pentane-1,2-diol and sodium oleoyl sarcosinate and optionally sodium lauryl sulfoacetate

Embodiment 4

Mixture according to embodiment 3, comprising
- 5 through 30 wt. %, preferably 10 through 20 wt. %, preferably 12 through 18 wt. %, particularly preferably 13 through 17 wt. % of pentane-1,2-diol,
- 5 through 30 wt. %, preferably 10 through 20 wt. %, preferably 12 through 18 wt. %, particularly preferably 13 through 17 wt. % of sodium oleoyl sarcosinate,
- optionally 3 through 22 wt. %, preferably 5 through 20 wt. %, preferably 8 through 20 wt. %, particularly preferably 11 through 17 wt. % of sodium lauryl sulfoacetate, wherein the percentages by weight refer in each case to the total mass of the mixture.

Embodiment 5

Mixture according to embodiment 3, characterized in that the weight ratio of pentane-1,2-diol to sodium oleoyl sarcosinate is in the range from 5:1 through 1:5, preferably in the range from 3:1 through 1:3, preferably in the range from 2:1 through 1:2, more preferably in the range from 3:2 through 2:3, particularly preferably in the range from 4:3 through 3:4, quite particularly preferably in the range from 8:7 through 7:8.

Embodiment 6

Mixture according to embodiment 3 or 4, comprising or consisting of
- 10 through 20 wt. %, preferably 12 through 18 wt. %, preferably 13 through 17 wt. %, particularly preferably 14 through 16 wt. % of pentane-1,2-diol,
- 10 through 20 wt. %, preferably 12 through 18 wt. %, preferably 13 through 17 wt. %, particularly preferably 13 through 16 wt. % of sodium oleoyl sarcosinate,
- 5 through 20 wt. %, preferably 8 through 18 wt. %, preferably 11 through 17 wt. %, particularly preferably 12 through 16.5 wt. % of sodium lauryl sulfoacetate,
- 25 wt. % or more of water, preferably 30 through 60 wt. % water, preferably 35 through 55 wt. % water,
- optionally sodium oleate, preferably 0.5 through 5 wt. % of sodium oleate, preferably 1 through 3 wt. %,
- optionally sodium chloride, preferably 1 through 5 wt. % of sodium chloride, preferably 1.5 through 4 wt. %,
- optionally disodium sulfoacetate, preferably 0.5 through 3 wt. %, preferably 0.6 through 2 wt. %,
- optionally sodium sulfate, preferably 0.5 through 3 wt. %, preferably 1 through 2 wt. %, wherein the percentages by weight refer in each case to the total mass of the mixture.

Embodiment 7

Mixture according to any of the embodiments 3 through 6, characterized in that the mixture has a pH value of 6 or higher, preferably a pH value of 6.5 or higher.

Embodiment 8

Composition for the production of a cosmetic preparation, preferably of a body care product, comprising a mixture according to any of the embodiments 3 through 7 and one or a plurality of organic substances with a log $K_{OW}$ value in the range from 1 through 12, preferably in the range from 2 through 10, particularly preferably in the range from 3 through 8.

Embodiment 9

Composition according to embodiment 8, characterized in that the composition is transparent, preferably has a turbidity of less than 10 NTU (nephelometric turbidity units), preferably of less than 5 NTU, particularly preferably of less than 3 NTU.

Embodiment 10

Composition according to embodiment 8 or 9, characterized in that the total amount of organic substance(s) with a log $K_{OW}$ value in the range from 1 through 12 is in the range from 0.1 through 5 wt. %, preferably in the range from 0.1 through 3 wt. %, preferably in the range from 0.15 through 1 wt. %, particularly preferably in the range from 0.2 through 0.8 wt. %, in each case relative to the total mass of the composition.

Embodiment 11

Cosmetic preparation, comprising
(i) a mixture according to any of the embodiments 3 through 7 and one or a plurality of organic substances with a log $K_{OW}$ value in the range from 1 through 12, preferably in the range from 2 through 10, particularly preferably in the range from 3 through 8
or
a composition according to any of the embodiments 8 through 10
and
(ii) optionally further cosmetically effective constituents,
(iii) optionally other constituents.

Embodiment 12

Cosmetic preparation according to embodiment 11, characterized in that the cosmetic preparation is selected from the group of body care products, and preferably is selected from the group consisting of aqueous and aqueous-alcoholic systems such as shower gels, shampoos, alcoholic perfumes, aqueous alcoholic perfumes, aftershave gels, creams, lotions, hair care products, hair styling products.

Embodiment 13

Cosmetic preparation according to embodiment 11 or 12, characterized in that the cosmetic preparation, preferably the body care product, comprises
0.1 through 15 wt. %, preferably 0.5 through 7 wt. %, more preferably 0.5 through 5 wt. %, and particularly preferably 1 through 3 wt. % of a mixture according to any of the embodiments 3 through 7
or
0.1 through 15 wt. %, preferably 0.5 through 7 wt. %, more preferably 0.5 through 5 wt. %, and particularly preferably 1 through 3 wt. % of a composition according to any of the embodiments 8 through 10
wherein the percentages by weight are in each case relative to the total mass of the cosmetic preparation.

Embodiment 14

Method of increasing the solubility of an organic substance and/or decreasing the turbidity of a preparation containing an organic substance and/or for increasing the transparency of a preparation containing one or a plurality of organic substances,
wherein the organic substance has in each case a log $K_{OW}$ value in the range from 1 through 12, preferably in the range from 2 through 10, particularly preferably in the range from 3 through 8,
comprising the step:
mixing the organic substance(s) with a mixture according to any of the embodiments 3 through 7.

Embodiment 15

Method of producing a mixture according to any of the embodiments 3 through 7, a composition according to any of the embodiments 8 through 10 or a cosmetic preparation according to any of the embodiments 11 through 13, comprising the step:
mixing of pentane-1,2-diol and sodium oleoyl sarcosinate and optionally sodium lauryl sulfoacetate.

Embodiment 16

Use of pentane-1,2-diol for improving the solubilizing action, in particular the dissolving power, of surfactants, preferably of sodium oleoyl sarcosinate, sodium lauryl sulfoacetate or mixture thereof, preferably a mixture of sodium oleoyl sarcosinate and sodium lauryl sulfoacetate in the weight ratio from 10:1 through 1:4, preferably in the weight ratio from 4:1 through 1:2.

The invention is explained in more detail below, on the basis of examples.

Examples

Unless stated otherwise, all figures given refer to weight.
The raw materials used in the following are commercially available.
The "Oleoyl sarcosinate HH" used in the following consisted of 54 wt. % of sodium oleoyl sarcosinate, 6 wt. % of sodium oleate and 40 wt. % water.
The "Lauryl sulfoacetate VV" used in the following contained about 67 wt. % of sodium lauryl sulfoacetate, about 14 wt. % of sodium chloride, 3-10 wt. % of disodium sulfoacetate and 7 wt. % of sodium sulfate and had a water content of less than 1.5 wt. %.

Example 1: Solubilizers (According to the Invention and Comparative Tests)

| Raw material | INCI | U.53787M wt. % | Z1 wt. % | Z2 wt. % |
|---|---|---|---|---|
| Oleoyl sarcosinate HH | Sodium oleoyl sarcosinate, sodium oleate | 25.00 | 25.00 | 25.00 |
| Hydrolite ® 5 (pentane-1,2-diol) | Pentylene glycol | 15.00 | 15.00 | 15.00 |
| 1,2-Propylene glycol | Propylene glycol | — | 15.00 | — |
| Glycerol | Glycerol | — | — | 15.00 |
| Lauryl sulfoacetate VV | Sodium lauryl sulfoacetate, sodium chloride, disodium sulfoacetate, sodium sulfate | 20.00 | 20.00 | 20.00 |
| Demineralized water | Aqua | To 100 | To 100 | To 100 |

The mixture according to the invention U.53787M (pH value: 5.5) was light yellow and clear (transparent), whereas the mixtures Z1 and Z2, not according to the invention, were cloudy and contained incompletely dissolved solid constituents. The mixture according to the invention U.53787M remained clear and stable over a storage time of 6 months in daylight and 5° C., 25° C. or 40° C.

Example 2: Mixtures According to the Invention (Solubilizers)

| Raw material | INCI | A wt. % | B wt. % | C wt. % |
|---|---|---|---|---|
| Oleoyl sarcosinate HH | Sodium oleoyl sarcosinate, sodium oleate | 25.00 | 25.00 | 25.00 |
| Hydrolite ® 5 (pentane-1,2-diol) | Pentylene glycol | 15.00 | 15.00 | 15.00 |
| Lauryl sulfoacetate VV | Sodium lauryl sulfoacetate, sodium chloride, disodium sulfoacetate, sodium sulfate | 20.00 | 20.00 | 20.00 |
| NaOH 50% in water | Sodium hydroxide | 1.11 | 1.55 | 2.00 |
| Demineralized water | Aqua | To 100 | To 100 | To 100 |
| pH value | | 6.0 | 6.5 | 7.5 |

These mixtures according to the invention were clear (transparent) and remained clear and stable over a storage time of 6 months in daylight. The mixtures according to the invention A, B and C showed a further improved dissolving power and even better solubilizing properties than U.53787M from example 1.

Example 3: Storage Stability of Compositions and Preparations According to the Invention The transparency (clarity) of the compositions was determined after 3 months at the constant storage temperature stated in each case.

Example 3.1: Investigations with Menthyl Lactate

| | wt. % | wt. % | wt. % |
|---|---|---|---|
| Frescolat ® ML (menthyl lactate) | 0.50 | 0.40 | 0.40 |
| Solubilizer U.53787M from example 1 | — | 2.00 | 2.00 |
| Solubilizer B from example 2 | 2.00 | — | — |
| Glycerol | 5.00 | 5.00 | — |
| Pentane-1,2-diol | — | — | 5.00 |
| 1,2-Propylene glycol | — | — | — |
| Water | To 100 | To 100 | To 100 |
| Assessment of turbidity | | | |
| Production at 25° | clear | clear | clear |
| Storage at 5° C. | clear | clear | clear |
| Storage at 40° C. | clear | clear | clear |

Example 3.2: Investigations with Dragocid® Liquid

| | wt. % | wt. % | wt. % | wt. % |
|---|---|---|---|---|
| Dragocid ® Liquid | 1.20 | 1.20 | 1.20 | 1.20 |
| Solubilizer U.53787M from example 1 | 2.00 | 2.00 | 2.00 | 2.00 |
| Glycerol | 5.00 | — | — | — |
| Pentane-1,2-diol | — | 0.50 | 3.00 | — |
| 1,2-Propylene glycol | — | — | 0.50 | 0.50 |
| Water | To 100 | To 100 | To 100 | To 100 |
| Assessment of turbidity | | | | |
| Production at 25° | clear | clear | clear | clear |
| Storage at 5° C. | clear | clear | clear | clear |
| Storage at 40° C. | clear | clear | clear | clear |

Dragocid® Liquid is a mixture of phenoxyethanol, methylparaben, ethylparaben, butylparaben, propylparaben and isobutylparaben, commercially available from Symrise.

Example 3.3: Investigations with Bisabolol

| | wt. % | wt. % | wt. % | wt. % |
|---|---|---|---|---|
| Bisabolol | 0.10 | 0.10 | 0.10 | 0.10 |
| Solubilizer U.53787M from example 1 | 2.00 | 2.00 | 2.00 | 2.00 |
| Pentane-1,2-diol | 0.50 | 2.50 | — | — |
| 1,2-Propylene glycol | — | — | 3.00 | 1.00 |
| Water | To 100 | To 100 | To 100 | To 100 |
| Assessment of turbidity | | | | |
| Production at 25° | clear | clear | clear | clear |
| Storage at 5° C. | clear | clear | clear | clear |
| Storage at 40° C. | clear | clear | clear | clear |

| | wt. % | wt. % |
|---|---|---|
| Bisabolol | 0.10 | 0.20 |
| Solubilizer U.53787M from example 1 | 2.00 | — |
| Solubilizer A from example 2 | — | 2.00 |
| Glycerol | 4.00 | 5.00 |
| Water | To 100 | To 100 |
| Assessment of turbidity | | |
| Production at 25° | clear | clear |
| Storage at 5° C. | clear | clear |
| Storage at 40° C. | clear | clear |

Example 3.4: Investigations with Other Organic Substances

| | wt. % |
|---|---|
| Organic substance to be investigated | "x.xx" |
| Solubilizer U.53787M from example 1 | 2.00 |
| Glycerol | 5.00 |
| Water | To 100 |
| Assessment of turbidity | |
| Production at 25° | clear |
| Storage at 5° C. | clear |
| Storage at 40° C. | clear |

The following organic substances to be investigated were incorporated in this framework formulation, in each case in an amount of "x.xx wt. %", wherein the respective composition or preparation remained clear and stable for the period of storage at the constant temperature stated in each case:

Sage oil (*Salvia officinalis* oil) (0.10 wt. %), rose oil (*Rosa Damascena* Flower Oil) (0.20 wt. %), perfume oil Lait de Rose (0.20 wt. %), perfume oil Lait Vitamine Sun (0.30 wt. %), perfume oil L'Eau d'été (0.20 wt. %), perfume oil Jasmin Flowers (0.30 wt. %), paraffin oil (paraffinum liquidum) (0.10 wt. %) or Crinipan® AD (climbazole anti-dandruff agent) (0.10 wt. %).

Formulation Examples

In the following formulation examples, the respective phase containing the PEG-free solubilizer U.53787M according to the invention from example 1 was clear and had a turbidity value of less than 3 NTU (as defined above).

The finished formulations of formulation examples F1 through F9 had a turbidity value of less than 10 NTU (as defined above) (examples F1, F2, F5, F7 and F9) or of less than 3 NTU (formulation examples F3, F4, F6 and F8). Only the yellowish-white emulsion of formulation example F10 had a turbidity value of >10 NTU.

Formulation Example F1: Aftershave Gel

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 7.00 |
|  | Hydrolite® 5 | Pentylene glycol | 5.00 |
|  | SymSitive® | Pentylene glycol, 4-t-butylcyclohexanol | 1.00 |
|  | Vitamin-E acetate | Tocopheryl acetate | 0.50 |
|  | Frescolat® ML | Menthyl lactate | 0.50 |
|  | Perfume | Fragrance | 0.15 |
|  | Glycerol | Glycerol | 5.00 |
| B | Water | Water (aqua) | To 100 |
|  | Pemulen® TR2 | Acrylates/C10-30 alkyl acrylate crosspolymer | 1.00 |
|  | Extrapone® Glacier Water GW | Glycerol, aqua | 1.00 |
|  | SymCalmin® | Butylene glycol, pentylene glycol, hydroxyphenyl propamidobenzoic acid | 0.50 |
|  | NaOH 10% in water | Sodium hydroxide | 3.15 |
| C | Tegosoft® PC41 | Polyglyceryl-4 caprate | 2.00 |
| D | Ethanol | Alcohol | 4.80 |
|  | Blue dye 1% in water | Color | 0.50 |

Production: Dissolve the ingredients of phase A with stirring until clear. For phase B, leave the thickener to swell in water, and add the remaining components with stirring. Add phase A to phase B with stirring, add phase C and phase D one after another with stirring.

The pH value of formulation example F1 was 5.9.

Formulation Example F2: Sunscreen Gel with Sun Protection Factor SPF 20-25

| Phase | Raw material | INCI | wt. % |
|---|---|---|---|
| A | Water | Water (aqua) | To 100 |
|  | Neo Heliopan® AP, 10% in water, neutralized with NaOH | Disodium phenyl dibenzimidazole tetrasulfonate | 30.00 |
|  | Neo Heliopan® hydro, 15% in water, neutralized with NaOH | Phenylbenzimidazole sulfonic acid | 33.34 |
|  | EDETA® BD | Disodium EDTA | 0.10 |
|  | Dragosine® | Carnosine | 0.20 |
| B | Esaflor HDR | Hydroxypropyl guar | 1.50 |
| C | Biotive® Troxerutin | Troxerutin | 1.60 |
|  | Red dye | Color | 0.10 |
| D | Hydrolite® 5 | Pentylene glycol | 5.00 |
|  | Perfume | Fragrance | 0.10 |
|  | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 0.50 |
|  | SymDiol® 68 | 1,2-Hexanediol, caprylyl glycol | 1.00 |

Production: Add the ingredients of phase A together. Add the thickener from phase B with stirring and leave to swell. Then add the components of phase C one after another with stirring. For phase D, dissolve the components until clear and add to phase A/B/C with stirring.

The pH value of formulation example F2 was 7.6.

Formulation Example F3: After Sun Gel

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 15.00 |
|  | Glycerol | Glycerin | 5.00 |
|  | Natural alpha-bisabolol | Bisabolol | 0.10 |
|  | Vitamin-E acetate | Tocopheryl acetate | 0.50 |
|  | Sym Repair® | Hexyldecanol, bisabolol, cetylhydroxyproline palmitamide, stearic acid, Brassica campestris sterols | 0.50 |
|  | SymHelios® 1031 | Benzylidene dimethoxydimethylindanone | 0.10 |
|  | Perfume | Fragrance | 0.20 |
| B | Water | Water (aqua) | To 100 |
|  | Pemulen® TR2 | Acrylates/C10-30 alkyl acrylate crosspolymer | 1.00 |
|  | D-Panthenol | Panthenol, aqua | 0.50 |
|  | Flowerpone® Frangipani | Aqua, pentylene glycol, PEG-40 hydrogenated castor oil, trideceth-9, bisabolol, Plumeria acutifolia flower extract | 1.00 |
|  | Extrapone® Pearl GW | Aqua, glycerol, hydrolyzed pearl, xanthan gum | 1.00 |
|  | NaOH 10% in water | Sodium hydroxide | 3.00 |
| C | Ethanol | Alcohol | 14.40 |

Production: Dissolve the ingredients of phase A with stirring until clear. For phase B, leave the thickener to swell in water, add the remaining components with stirring. Add phase A to phase B with stirring, add phase C with stirring.

The pH value of formulation example F3 was 5.8.

Formulation Example F4: Clear Body Tonic

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 7.00 |
|  | Frescolat ® ML | Menthyl lactate | 0.80 |
|  | Perfume | Fragrance | 1.00 |
| B | Water | Water (aqua) | To 100 |
|  | Hydrolite ® 5 | Pentylene glycol | 5.00 |
|  | Extrapone ® Bamboo | Propylene glycol, aqua, butylene glycol, *Bambusa vulgaris* shoot extract | 1.00 |
|  | Extrapone ® Guarana | Aqua, propylene glycol, *Paullinia cupana* seed extract, alcohol | 1.00 |
| C | Ethanol | Alcohol | 25.00 |
|  | Azorubin 0.1% | Color | 0.10 |

Production: Dissolve the ingredients of phase A with stirring until clear. Mix the components of phase B and add to phase A with stirring, add phase C one after another with stirring.

The pH value of formulation example F4 was 6.0.

Formulation Example F5: Self Tan Gel

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 15.00 |
|  | Vitamin E acetate | Tocopheryl acetate | 0.50 |
|  | Alpha-Bisabolol Natural | Bisabolol | 0.10 |
|  | SymHelios ® 1031 | Benzylidene dimethoxydimethylindanone | 0.10 |
|  | Hydrolite ® 5 | Pentylene glycol | 2.50 |
|  | Glycerol | Glycerin | 5.00 |
|  | Perfume | Fragrance | 0.20 |
| B | Water | Water (aqua) | To 100 |
|  | Pemulen ® TR2 | Acrylates/C10-30 alkyl acrylate crosspolymer | 1.00 |
|  | Dihydroxyacetone | Dihydroxyacetone | 5.00 |
|  | D-Panthenol | Panthenol | 0.50 |
|  | Extrapone ® Lotus Flower | Aqua, butylene glycol, *Nelumbo nucifera* flower extract | 1.00 |
|  | NaOH 10% in water | Sodium hydroxide | 0.70 |
| C | Ethanol | Alcohol | 5.00 |

Production: Dissolve the ingredients of phase A with stirring until clear. For phase B, leave the thickener to swell in water, add the remaining components with stirring. Add phase A to phase B with stirring, add phase C with stirring.

The pH value of formulation example F5 was 5.0.

Formulation Example F6: Impregnating Solution for Baby Wipes

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 10.00 |
|  | Natural alpha-bisabolol | Bisabolol | 0.10 |
|  | Vitamin-E acetate | Tocopheryl acetate | 0.50 |
|  | Hydrolite ® 5 | Pentylene glycol | 5.00 |
|  | Glycerol | Glycerin | 5.00 |
|  | Tegosoft ® PC41 | Polyglyceryl-4 caprate | 1.00 |
| B | Water | Water (aqua) | To 100 |
|  | D-Panthenol | Panthenol, aqua | 0.80 |
|  | DragoCalm ® | Aqua, glycerin, *Avena sativa* kernel extract | 1.00 |
|  | Allplant Essence ® Org Rose *Geranium P* | *Pelargonium graveolens* flower/leaf/stem water | 1.00 |

Production: Dissolve the ingredients of phase A with stirring until clear. Mix the components of phase B and add to phase A with stirring.

The pH value of formulation example F6 was 6.2.

Formulation Example F7: Alcohol-Free Body Gel

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 10.00 |
|  | Orange Oil Guinea | Citrus aurantium dulcis | 0.25 |
|  | Croatian Lavender Oil | *Lavandula hybrida* oil | 0.10 |
|  | Hydrolite ® 5 | Pentylene glycol | 5.00 |
|  | Vitamin-E acetate | Tocopheryl acetate | 0.50 |
|  | Tegosoft ® PC41 | Polyglyceryl-4-caprate | 2.00 |
| B | Water | Water (aqua) | To 100 |
|  | Keltrol ® CG-T | Xanthan gum | 0.50 |
|  | Aristoflex ® TAC | Ammonium acryloyl dimethyltaurate/carboxyethyl acrylate crosspolymer | 1.50 |
|  | *Aloe Vera* Gel Concentrate 10/1 | *Aloe barbadensis* gel | 0.50 |
|  | Dragosine ® | Carnosine | 0.10 |
|  | SymGlucan ® | Aqua, glycerin, beta-glucan | 2.00 |
|  | D-panthenol | Panthenol, aqua | 0.50 |
|  | "Orange No. 4" dye 0.1% | Color | 0.10 |

Production: Dissolve the ingredients of phase A with stirring until clear. For phase B, leave the thickener to swell in water, add the remaining components with stirring. Add phase A to phase B with stirring.

The pH value of formulation example F7 was 6.0.

Formulation Example F8: Cosmetic Preparation with Plant Extracts

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 10.00 |
|  | Milfoil Oil | *Achillea millefolium* oil | 0.10 |
|  | Egyptian Chamomile Oil | *Chamomilla recutita* flower oil | 0.20 |
|  | Natural alpha-bisabolol | Bisabolol | 0.10 |
| B | SymDiol® 68 | 1,2-Hexanediol, caprylyl glycol | 0.50 |
|  | 1,2-Butylene glycol | Butylene glycol | 40.00 |
| C | Water | Water (aqua) | To 100 |

Production: Dissolve the ingredients of phase A with stirring until clear. Mix the components of phase B and add to phase A with stirring. Add phase C with stirring.

The pH value of formulation example F8 was 6.2.

Formulation Example F9: Styling Gel

| Phase | Raw material | INCI | wt. % |
|---|---|---|---|
| A | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 7.00 |
|  | Hydrolite® 5 | Pentylene glycol | 2.50 |
|  | SymRepair® | Hexyldecanol, bisabolol, cetylhydroxyproline palmitamide, stearic acid, *Brassica campestris* sterols | 1.00 |
|  | Perfume | Fragrance | 0.30 |
| B | Water | Water (aqua) | To 100 |
|  | Amaze™ XT | Dehydroxanthan gum | 2.00 |
|  | Hubridur® 875 | Polyurethane-2 and polymethyl methacrylate | 5.00 |
|  | Dragoderm® | Glycerin, *Triticum vulgare* gluten, aqua | 2.00 |
|  | Extrapone® Silk | Aqua, glycerin, hydrolyzed silk | 1.00 |
|  | Symdiol® 68 | 1,2-Hexanediol, caprylyl glycol | 1.00 |
| C | Ethanol | Alcohol | 5.00 |

Production: Dissolve the ingredients of phase A with stirring until clear. For phase B, leave the thickener to swell in water, add the remaining components with stirring. Add phase A to phase B with stirring, add phase C with stirring.

The pH value of formulation example F9 was 6.6.

Formulation Example F10: Sunscreen Emulsion

| Phase | Raw material | INCI | wt. % |
|---|---|---|---|
| A | Emulsiphos® | Potassium cetyl phosphate, hydrogenated palm glycerides | 2.50 |
|  | Cithrol™ GMM | Glyceryl myristate | 1.00 |
|  | Neo Heliopan® 357 | Butyl methoxydibenzoylmethane | 5.00 |
|  | Neo Heliopan® OS | Ethylhexyl salicylate | 5.00 |
|  | Neo Heliopan® 303 | Octocrylene | 10.00 |
|  | Neo Heliopan® HMS | Homosalate | 10.00 |
|  | Tinosorb® S | Bis-ethylhexyloxyphenol methoxyphenyl triazine | 4.00 |
|  | Neo Heliopan® E 1000 | Isoamyl p-methoxycinnamate | 2.00 |
|  | Dragoxat® 89 | Ethylhexyl isononanoate | 3.00 |
|  | SymMollient® S | Cetearyl nonanoate | 2.00 |
|  | Antaron - Ganex® WP 660 | Tricontanyl PVP | 2.00 |
|  | Xiameter® PMX-0246 cyclosiloxane | Cyclohexasiloxane (and) cyclopentasiloxane | 2.00 |
|  | KF-995 | Cyclopentasiloxane | 2.00 |
|  | Silcare® Silicone 41M65 | Stearyl dimethicone | 1.00 |
|  | EDETA® BD | Disodium EDTA | 0.10 |
|  | Vitamin E acetate | Tocopheryl acetate | 0.50 |
|  | Asensa™ PR 200 | Polyethylene | 1.00 |
|  | Keltrol® CG-T | Xanthan gum | 0.50 |
|  | Eusolex® T-AVO | Titanium dioxide, silica | 2.00 |
| B | Water | Aqua (water) | 21.86 |
|  | Neo Heliopan® Hydro, 15% in water, neutralized with NaOH | Phenylbenzimidazole sulfonic acid | 13.34 |
|  | Glycerol | Glycerin | 3.00 |
|  | D-Panthenol 75L | Panthenol | 0.60 |
|  | NaOH 10% in water | Sodium hydroxide | 0.90 |
|  | PEG-free solubilizer U.53787M from example 1 | Aqua, pentylene glycol, sodium lauryl sulfoacetate, sodium oleoyl sarcosinate, sodium chloride, disodium sulfoacetate, sodium oleate, sodium sulfate | 2.00 |
| C | Phenoxyethanol | Phenoxyethanol | 0.75 |
|  | SymClariol® | Decylene glycol | 0.25 |
| D | Perfume | Fragrance | 0.20 |
|  | Orgasol® Caresse | Polyamide-5 | 1.50 |

Production: Dissolve the ingredients of phase A and of phase B separately at 80° C. and add together with stirring. Add phase C at 60° C. to phase A/B with stirring and then homogenize. Leave to cool to room temperature, with stirring. Add phase D and homogenize again.

The pH value of formulation example F10 was 7.3.

The invention claimed is:

1. A method of
  increasing the solubility of one or a plurality of organic substances,
  decreasing the turbidity of a preparation containing one or a plurality of organic substances,
  increasing the transparency of a preparation containing one or a plurality of organic substances,
  wherein the organic substances have in each case a log $K_{OW}$ value in the range from 1 through 12, comprising the step of:
  mixing the one or more organic substances with a solubilizer mixture comprising:
  (i) one or more 1,2-alkane diols comprising 5-8 carbon atoms,
  (ii) one or more ammonium-, sodium- or potassium-$R^{alk}$-sarcosinates, wherein $R^{alk}$ is alkanoyl, alkenoyl or alkadienoyl comprising 12-22 carbon atoms, and
  (iii) optionally one or more sodium- or potassium-$C_{10}$-$C_{16}$-alkyl-sulfoacetates.

2. The method of claim 1, wherein the preparation is a dispersion and/or an emulsion.

3. The method of claim 1, wherein the solubilizer mixture comprises:
   (i) one or more 1,2-alkane diols comprising 5-8 carbon atoms,
   (ii) one or more ammonium-, sodium- or potassium-$R^{alk}$-sarcosinates, wherein $R^{alk}$ is alkanoyl, alkenoyl or alkadienoyl comprising 12-22 carbon atoms, and
   (iii) one or more sodium- or potassium-$C_{10}$-$C_{16}$-alkyl-sulfoacetates.

4. The method of claim 1, wherein the solubilizer mixture comprises:
   (i) one or more 1,2-alkane diols comprising 5-8 carbon atoms, in an amount of from 5 to 30 weight %,
   (ii) one or more ammonium-, sodium- or potassium-$R^{alk}$-sarcosinates, wherein $R^{alk}$ is alkanoyl, alkenoyl or alkadienoyl comprising 12-22 carbon atoms, in an amount of from 5 to 30 weight %, and
   (iii) optionally one or more sodium- or potassium-$C_{10}$-$C_{16}$-alkyl-sulfoacetates in an amount of from 3 to 22 weight %.

5. The method of claim 1, wherein the solubilizer mixture comprises:
   (i) one or more 1,2-alkane diols comprising 5-8 carbon atoms, in an amount of from 10 to 20 weight %,
   (ii) one or more ammonium-, sodium- or potassium-$R^{alk}$-sarcosinates, wherein $R^{alk}$ is alkanoyl, alkenoyl or alkadienoyl comprising 12-22 carbon atoms, in an amount of from 10 to 20 weight %, and
   (iii) optionally one or more sodium- or potassium-$C_{10}$-$C_{16}$-alkyl-sulfoacetates in an amount of from 5 to 20 weight %.

6. The method of claim 4 wherein (i) is one or more linear 1,2-alkane diols comprising 5-8 carbon atoms.

7. The method of claim 4 wherein (i) is one or more of 1,2-pentanediol, 1,2-hexanediol and 1,2-octanediol.

8. The method of claim 4 wherein (i) is 1,2-pentanediol.

9. The method of claim 4 wherein (ii) is one or more ammonium-, sodium- or potassium-$R^{alk}$-sarcosinates, wherein $R^{alk}$ is alkanoyl, alkenoyl or alkadienoyl comprising 16-22 carbon atoms.

10. The method of claim 4 wherein (ii) is one or more selected from the group consisting of sodium myristoyl sarcosinate, potassium palmitoyl sarcosinate, sodium stearoyl sarcosinate, sodium oleoyl sarcosinate, potassium oleoyl sarcosinate, sodium linoleoyl sarcosinate, potassium lauroyl sarcosinate, potassium cocoyl sarcosinate, sodium cocoyl sarcosinate, ammonium lauroyl sarcosinate, and ammonium cocoyl sarcosinate.

11. The method of claim 4 wherein (ii) is one or more selected from the group consisting of sodium myristoyl sarcosinate, potassium palmitoyl sarcosinate, sodium stearoyl sarcosinate, sodium oleoyl sarcosinate, potassium oleoyl sarcosinate, and sodium linoleoyl sarcosinate.

12. The method of claim 4 wherein (ii) is sodium oleoyl sarcosinate.

13. The method of claim 4 wherein (iii) is present and is one or more sodium- or potassium-$C_{10}$-$C_{14}$-alkyl-sulfoacetates.

14. The method of claim 4 wherein (iii) is present and is selected from the group consisting of sodium lauryl sulfoacetate, potassium lauryl sulfoacetate, sodium myristyl sulfoacetate, and potassium myristyl sulfoacetate.

15. The method of claim 4 wherein (iii) is sodium lauryl sulfoacetate.

16. The method of claim 1, wherein (i) is 1,2-pentanediol, and (ii) is sodium oleoyl sarcosinate.

17. The method of claim 4 wherein (i) is 1,2-pentanediol, (ii) is sodium oleoyl sarcosinate and (iii) is sodium lauryl sulfoacetate.

* * * * *